United States Patent [19]

Ishikawa et al.

[11] Patent Number: 4,465,859
[45] Date of Patent: Aug. 14, 1984

[54] N,N-DIALKYL-3-OXO-3-ALKYL-1,2-DIFLUOROPROPENYLAMINE

[75] Inventors: Nobuo Ishikawa, Yokohama; Tomoya Kitazume, Tokyo, both of Japan

[73] Assignee: Daikin Kogyo Co., Ltd., Osaka, Japan

[21] Appl. No.: 528,117

[22] Filed: Aug. 31, 1983

[30] Foreign Application Priority Data

Aug. 31, 1982 [JP] Japan .................. 57-151005

[51] Int. Cl.³ .............................. C07C 87/26
[52] U.S. Cl. .................................... 564/502
[58] Field of Search ......................... 564/502

[56] References Cited

U.S. PATENT DOCUMENTS 2,198,260  4/1940  van Melsen .............. 564/502 X
2,228,039  1/1941  van Peski et al. ......... 564/502 X
3,839,415  10/1974  Easton et al. ............ 564/502 X Primary Examiner—Paul F. Shaver
Attorney, Agent, or Firm—Armstrong, Nikaido, Marmelstein & Kubovcik

[57] ABSTRACT

N,N-dialkyl-3-oxo-3-alkyl-1,2-difluoropropenylamine expressed by the following general formula:

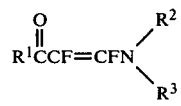

where $R^1$, $R^2$ and $R^3$ are same or different alkyl groups.

2 Claims, No Drawings

N,N-DIALKYL-3-OXO-3-ALKYL-1,2-DIFLUOROPROPENYLAMINE

BACKGROUND OF THE INVENTION

1. Field of the Invention

The present invention relates to a new and useful compound N,N-dialkyl-3-oxo-3-alkyl-1,2-difluoropropenylamine.

2. Description of the Prior Art

Generally, the fluorine containing compounds have useful applications in many fields because of their chemical stability, resistance to other chemicals, weatherproof property, water and oil repellent property, physiological activities, etc. Among others, those that have an unsaturated carbon-carbon double bond are particularly useful for the monomer used in the manufacture of fluorine containing polymer.

OBJECTS AND SUMMARY OF THE INVENTION

An object of the present invention is to provide a new and useful amine comprising a fluorine containing unsaturated group.

Namely, the invention provides an N,N-dialkyl-3-oxo-3-alkyl-1,2-difluoropropenylamine expressed by the following general formula:

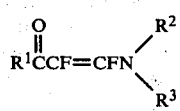

where $R^1$, $R^2$ and $R^3$ are same or different alkyl groups.

Containing a fluorine atom in its molecule, the above propenylamine is endowed with the characteristic properties of the fluorine containing compound while the presence of an unsaturated bond in its molecule makes it useful as a constituent monomer of the fluorine containing polymer based on addition polymerization.

In the above general formula of the propenylamine embodying the invention, $R^1$, $R^2$ and $R^3$ may be selected from among alkyl groups having up to 10 carbon atoms and preferably up to 5 carbon atoms, for example, methyl, ethyl, propyl, isopropyl, butyl, and isobutyl groups.

DESCRIPTION OF THE PREFERRED EMBODIMENTS

The above new compound embodying the invention will be described below in terms of its manufacturing method.

For example, 4-chloro-3,4,4-trifluoro-2-1-butanone 1 is used as the starting material to react with two equivalents of diethylamine according to the formula given below. The reaction with the first molecule of diethylamine gives an intermediate product methyl trifluorovinyl ketone 2, to which the second molecule of diethylamine is added by the Michael reaction to produce the intended products N,N-diethyl-3-oxo-3-methyl-1,2-difluoropropenylamine 3 and N,N-diethyl-3-oxo-3-methyl-1,1,2-trifluoropropylamine (or N,N-diethyl-3-oxo-1,1,2-trifluorobutylamine) 4.

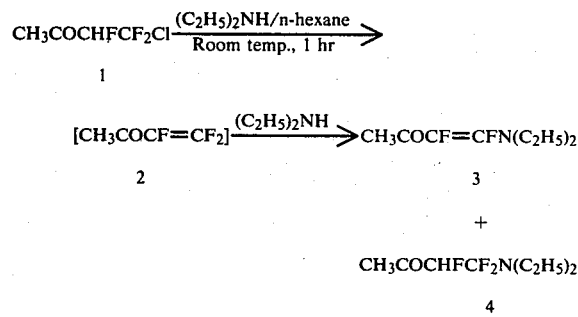

The reaction gives the above products 3 and 4 at a total yield of 85% from the starting material 1. More than 99% of the products are accounted for by 3 (so-called "enamine") and 4 is produced only in a trace.

The products that are fluid (b.p. 82°–83° C./2 mmHg) gives the following data on analysis:

3 (E form):
  NMR
    F (bonded to C on COCH₃ side):
      Chemical shift 107.5 (d) (from ext. trifluoroacetic acid)
    F (bonded to C on N(C₂H₅)₂ side):
      δ28.1, coupling constant 103.3 Hz 3 (Z form):
  NMR
    F (bonded to C on COCH₃ side):
      Chemical shift 95.5 (d,q),
      Coupling constant 11.1 Hz
      Coupling constant with H on CH₃CO 5.5 Hz
    F (bonded to C on N(C₂H₅)₂ side):
      9.4 ppm (d,d,d)
    H(COCH₃):
      Chemical shift δ2.12, 2.08,
      Coupling constant 5.5 Hz
    H(CH₃):
      Chemical shift 1.23
    H(N(C₂H₅)₂):
      Coupling constant 3.8, 2.8 Hz It is noted that the starting material 1 can be synthesized at a yield of 82% by the following formula:

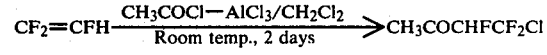

The enamine 3 that was prepared with a trace of the compound 4 as mentioned above was then tried to fluorinate various alcohols. The results showed that of the two products the compound 4 is a fluorine source (fluorinating agent) that can contribute to fluorination as mentioned below.

Among alcohols subjected to fluorination, ordinary primary alcohols gave no fluorinated product, except for benzyl alcohol, each being converted to a stoichiometric amount of an unsaturated compound 5 according to the following formula:

-continued $$(C_2H_5)_2NC(OR)=CFCOCH_3$$
5

($^{19}$F NMR yield app. 100%)

where for R—OH, $C_2H_5OH$, n—$C_8H_{17}OH$ and $(CH_3)_3CCH_2OH$ were used. This behavior is very different from the FAR reagent $(C_2H_5)_2NCF_2CHFCl$ which is a fluorinating agent heretofore in use.

With benzyl alcohol, however, the compound 4 gave the fluorinated product (PhCH$_2$F) of this alcohol in a comparatively high yield though dibenzyl ether was also produced as a by-product. Further, secondary and tertiary alcohols as listed in the following table could be fluorinated with the compound 4 as with the FAR reagent according to the following formula, each giving a corresponding fluroinated product 6:

$$R'-OH + (C_2H_5)_2NCF_2CHFCOCH_3 \xrightarrow[(C_2H_5)_2O]{Room\ temp.} R'-F +$$
4

6

Alkene + R'$_2$O + $(C_2H_5)_2NCOCHFCOCH_3$

| R'—OH | Reaction time (hr) | Yield* of R'—F, % |
|---|---|---|
| PhCH$_2$OH | 0.2 | 56 |
| PhCH(OH)C$_2$H$_5$ | 1 | 64 |
| PhC(OH)(CH$_3$)$_2$ | 10 | 55 |
| sec-butyl alcohol | 6 | 46 |
| tert-butyl alcohol | 14 | 51 |

*$^{19}$F NMR yield

In the above fluorination reaction, secondary and tertiary alcohols give an alkene as a by-product. By monitoring the reaction process of alcohol fluorination by the $^{19}$F NMR spectroscopy, it was found that the reaction proceeds through an intermediate product $(C_2H_5)_2NC(OR')=CFCOCH_3$ 5. In this case, a possible hypothesis is that 2 fluorine atoms that are bonded to a carbon atom next to the nitrogen atom as in 4 contribute to the formation of the above intermediate product and thereby facilitate the fluorination of alcohol.

It is noted that in the above embodiments, the methyl group of the starting material 1 and the ethyl groups of diethyl amine can be replaced with other alkyl groups, and particularly those having up to 10 carbon atoms, corresponding to groups R$^1$, R$^2$ and R$^3$ of the foregoing general formula. It is also noted that other secondary and tertiary alcohols can be used in the above fluorination reaction.

The above embodiments are set forth as a further description but are not to be construed as limiting the invention thereto. Various modifications and variations are possible without departing from the spirit and scope of the invention.

The invention will be understood more clearly with reference to the following Examples:

EXAMPLE 1

Into a mixture of 8.03 g (50 mmol) of 4-chloro-3,4,4-trifluoro-2-butanone and 200 ml of hexane, added dropwise a solution of 8.05 g (110 mmol) of diethyl-amine in 100 ml of hexane.

Keeping the vessel in an ice-bath. After 30 min. of stirring at room temperature the reaction mixture was filtered to remove crystals of diethylamine hydrochloride. The solvent was evaporated and the residual matter was subjected to vaccum distillation afording 7.40 g (84%) of N,N-diethyl-3-oxo-3-methyl-1,2-difluoropropenylamine.

EXAMPLE 2

Instead of diethylamine in EXAMPLE 1, 9.37 g (110 mmol) of piperidine was used.

N-(3-oxo-3-methyl-1,2-difluoro propenyl) piperidine was obtained in 90% yield by the simillar procedure to Example 1.

EXAMPLE 3

Into a mixture of 50 ml of diglyme and 8.03 g (50 mmol) of 4-chloro-3,4,4-trifluoro-2-butanone, 5.06 g (50 mmol, 1.0 eg.) of triethylamine was added dropwise in an icecooled bath. After this addition, the reaction mixture was stirred for 30 minutes at room temperature, resulting methyl trifluorovinylketone was trapped into an acetonedry ice bath under reduced pressure. This trapped product was added by 3.66 g (50 mmol) of diethylamine at $-78°$ C., then returned slowly to room temperature. After stirred at room temperature for 20 minutes, N N-diethyl-3-oxo-3-methyl-1,2-difluoropropenylamine was obtained in a yield of 10 to 30% together with CH$_3$COCHFCH$_3$ as a byproduct (yield 50 to 70%).

What is claimed is:
1. N,N-dialkyl-3-oxo-3alkyl-1,2-difluoropropenylamine as expressed by a general formula:

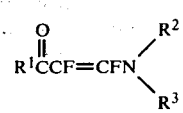

where R$^1$, R$^2$ and R$^3$ are same or different alkyl groups.
2. A propenylamine as claimed in claim 1 wherein the groups R$^1$, R$^2$ and R$^3$ have up to 10 carbons atoms each.

* * * * *